United States Patent [19]

Chambers et al.

[11] Patent Number: 5,705,713
[45] Date of Patent: Jan. 6, 1998

[54] PREPARATION OF FLUORO COMPOUNDS

[75] Inventors: Owen Ross Chambers, Filton; Patrick Charles Youmans, Longwell Green, both of United Kingdom

[73] Assignee: Rhone-Poulenc Chemicals Limited, Hertfordshire, United Kingdom

[21] Appl. No.: 545,844

[22] PCT Filed: May 12, 1994

[86] PCT No.: PCT/GB94/01023

§ 371 Date: Dec. 12, 1995

§ 102(e) Date: Dec. 12, 1995

[87] PCT Pub. No.: WO94/26756

PCT Pub. Date: Nov. 24, 1994

[30] Foreign Application Priority Data

May 12, 1993 [GB] United Kingdom .......... 9309795

[51] Int. Cl.⁶ .................................... C07C 22/00
[52] U.S. Cl. ................. 568/669; 568/677; 568/842
[58] Field of Search ...................... 568/669, 677, 568/842

[56] References Cited

FOREIGN PATENT DOCUMENTS

0495225A1  1/1992  European Pat. Off. .

OTHER PUBLICATIONS

Chemical Abstracts vol. 91:#140295b; Feiring et al., 1979.
Kirk–Othmer;Encycl.Chemical Technology;vol. 10;pp. 871–874, 1980.
Belluci et al;J.Chem.Soc.;Perkin Trans. II; vol. 10; pp. 1336–1340, 1981.
Tann et al; J.Org.Chem.50(19) pp. 3644–3647, 1985.
Journal of Medicinal Chemistry, vol. 32, No. 8, Aug. 1989, Washington U.S. pp. 1743–1749, A. Van Aerschot et al, "'3'-Fluoro–2',3'–dideoxy–5–chlorouridine: Most Selective Anti–HIV–1 Agent Among A Series of New 2'–and 3'–Fluorinated 2',3'–Dideoxynucleoside Analogues".
Chemical Reviews, vol. 92, No. 4, Jun. 1992, pp. 505–519, J.A. Wilkinson, "Recent Advances in the Selective Fluorination of the C–F Bond".
Chemical Reviews, vol. 92, No. 8, Dec. 1992, pp. 1745–1768, D.M. Huryn et al, "AIDS–Driven Nucleoside Chemistry", p. 1751, col. 2, line 6—p. 1752, col. 1, line 6, p. 1755, col. 2, line 15—p. 1756, col. 2, line 21.

*Primary Examiner*—Gary Geist
*Assistant Examiner*—Sreeni Padmanabhan
*Attorney, Agent, or Firm*—Burns, Doane, Swecker & Mathis, L.L.P.

[57] ABSTRACT

Fluoro compounds are made by reaction of an activated oxy-acid ester or cyclic ether starting material with hydrogen fluoride in the presence of an organometallic compound.

16 Claims, No Drawings

PREPARATION OF FLUORO COMPOUNDS

This is the U.S. National Stage Application of PCT/GB94/01023 filed May 12, 1994 now WO94/26756 published Nov. 24, 1994.

This invention relates to the preparation of fluoro-compounds, and more particularly to the preparation of fluoro-sugars (fluorinated carbohydrates).

Interest in organofluorine compounds partly derives from the fact that replacement of hydrogen by fluorine in naturally occurring compounds alters their biological properties dramatically. For example 9α-fluoro-hydrocortisone exhibits enhanced corticoid activity compared with the corresponding 9α-hydroxy compound. The selective introduction of fluorine into naturally occurring compounds and organic compounds having functional groups has, in general, presented the synthetic chemist with a continuous challenge.

For a review of methods for making fluorinated carbohydrates, for example, see A. A. E. PENGLIS, Advances in Carbohydrate Chemistry and Biochemistry, 38, 195 to 285 (1981), or for making fluorinated nucleosides, see D. M. HURYN and M. OKAE, Chem. Rev., 1992, 92, 1745 to 1768, and for recent advances in the selective formation of the C-F Bond, see J. A. WILKINSON, Chem. Rev. 1992, 92, 505 to 519.

Disclosures of using HF as source of fluorine in presence of a catalyst are very limited and only a few examples are described in the literature.

European Specification EP-A-0470355 describes a process for the preparation of 2'- and 3'-fluoro-2',3'-dideoxy-nucleosides by reaction of a corresponding anhydro dideoxy-nucleoside with hydrogen fluoride in the presence of an aluminium-containing catalyst. The catalyst may be, for example, aluminium acetylacetonate.

East German Specification 103241 describes the preparation of 3'-fluoro-2',3'-dideoxy-uridine by reaction of the corresponding 5-O-mesyl anhydronucleoside with hydrogen fluoride in the presence of an aluminium fluoride catalyst, followed by removal of the mesyl group.

The use of aluminium-containing compounds in the preparation of drugs has attracted unfavourable criticism because of the possible involvement of aluminium in the progress of Alzheimer's disease. It is therefore desirable to provide catalysts for the aforesaid reaction which do not contain aluminium. There is also a general need for catalysts which permit direct use of cheap hydrogen fluoride as the source of fluorine and give a more rapid reaction and/or a higher yield of the desired product, compared with existing techniques.

It has now been found that certain organo-metal compounds are highly effective in promoting the preparation of fluoro-compounds by reaction of a reactive oxy-acid ester or a reactive cyclic ether (other than an anhydrouridine) with hydrogen fluoride. In accordance with the present invention this reaction is carried out under anhydrous condition in the presence of an organometallic compound of formula:

$$MY_mZ_n \qquad (I)$$

where M is a 4-, 6- or 8- coordinated metal selected from magnesium, zinc, zirconium, cerium, titanium and iron, Y is a monodentate ligand, Z is a bidentate ligand or a cyclopentadienyl ligand, and m and n are each zero or positive integers such that (m+2 n)=4, 6 or 8.

In one embodiment of the invention the new process may be used to convert a reactive oxy-acid ester of formula $$R_1R_2CHOX \qquad (II)$$

into a fluoride of formula:

$$R_1R_2CHF \qquad (III)$$

wherein X is a sulphonic acid residue and $R_1$ and $R_2$ are each hydrogen or alkyl of 1 to 6 carbon atoms, the said alkyl radicals being optionally linked to form a 4 to 7 membered ring and being unsubstituted or substituted by phenyl, halogen, hydroxy or alkoxy of 1 to 6 carbon atoms.

X may be, for example

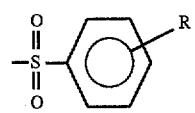

(where R=alkyl with 1 to 4 carbon atoms)

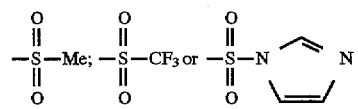

One example of a reaction of this kind is the transformation

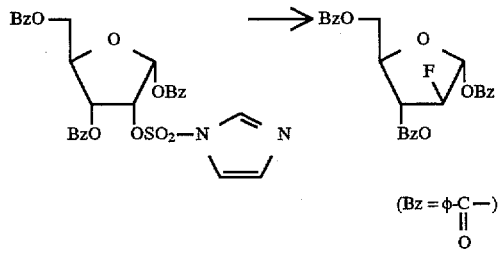

$$(Bz = \phi\text{-}\underset{\underset{O}{\|}}{C}\text{—})$$

The product is an intermediate for drugs used to the treatment of AIDS (C. H. TANN et al, J. Org. Chem, 1985, 50, 3644). Another example is the displacement of a primary sulfonyloxy group by fluorine as in:

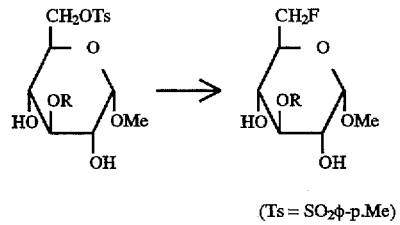

(Ts = SO$_2\phi$-p.Me)

Another example is the displacement of secondary sulfonyloxy groups, as in:

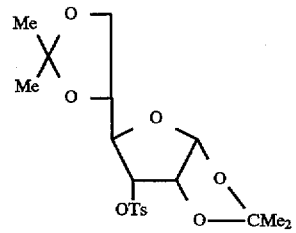

-continued

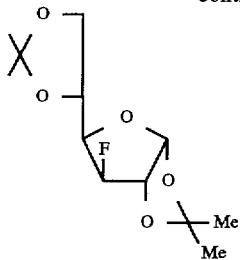

The process of the invention may also be applied to epoxides as in the reaction:

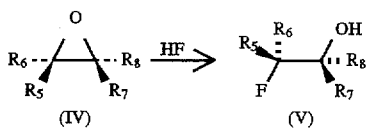

wherein $R_5$, $R_6$, $R_7$, $R_8$ may be the same or different, and each represents hydrogen, alkyl of 1 to 12 carbon atoms, optionally linked to form a 4- to 7-membered ring, and unsubstituted or substituted by alkyl, aryl or aralkyl substituents.

The starting material may be, for example, cyclohexene oxide:

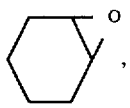

or propylene oxide

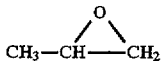

or a sugar epoxide, e.g.

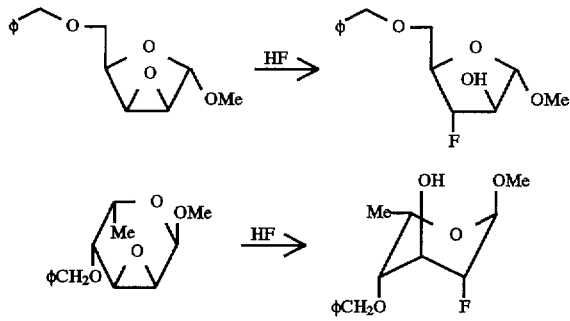

[an intermediate for tetracyclines derivative as mentioned in Japanese Patent 63-141992 (1988)].

The process of the invention is carried out under anhydrous conditions and preferably in the presence of an inert organic solvent, preferably an aprotic solvent, e.g. 1,4-dioxane, tetrahydrofuran, 1,2-dimethoxyethane, or bis(2-methoxyethyl)ether. The use of 1,4-dioxane is preferred.

The organometallic compound of formula I may be any suitable derivative of magnesium, zinc, zirconium, cerium, titanium or iron which is at least partially soluble in the reaction medium. The ligand Y is preferably halogen (e.g. fluorine or chlorine), alkoxy of 1 to 4 carbon atoms which may be halogenated (e.g. methoxy, ethoxy, isopropoxy or 2,2,2-trifluoroethoxy), or phenoxy which may optionally be substituted by alkyl of 1 to 4 carbon atoms, halogen (e.g. chlorine), or nitro. The ligand Z is preferably a carboxylato radical derived from an alkanoic acid of up to 12 (preferably 1 to 6) carbon atoms which may be halogenated (e.g. acetic acid) or benzoic acid which may optionally be substituted by alkyl of 1 to 4 carbon atoms, halogen (e.g. chlorine) or nitro. Z may also be derived from an alkanesulphonic acid of 1 to 12 (preferably 1 to 4) carbon atoms. Alternatively, the ligand Z may be β-diketo residue of a compound of formula R'—COCH$_2$CO-R" where R' is alkyl or haloalkyl (including perfluoroalkyl) of 1 to 4 carbon atoms (e.g. methyl) and R" is hydrogen, hydroxy, alkyl or haloalkyl (including perfluoroalkyl) of 1 to 4 carbon atoms, or alkoxy of 1 to 4 carbon atoms, and more especially methyl or ethoxy. Z may also be a cyclopentadienyl hydrocarbon ligand or alkyl-substituted derivative thereof (in which the alkyl has 1 to 4 carbon atoms); e.g. the organometallic compound may be bis(cyclopentadienyl) titanium dichloride, or bis (cyclopentadienyl) zirconium dichloride.

Preferred organometallic compounds for use in the present invention contain iron (III), in which case m is preferably zero, n is preferably 3, and Z is preferably a β-diketo residue, e.g. acetylacetonato. The use of iron (III) acetylacetonate is especially preferred.

The proportions of the starting materials and organometallic compound are not critical. An excess of the hydrogen fluoride, e.g. from 2 to 20 moles per mole of starting material, is generally used.

The proportion of the organometallic compound is generally approximately equimolar with the starting material, e.g. 0.5 to 2.0 moles of the organometallic compound (on the basis of its metal content) per mole of starting material. The reaction is conveniently carried out with moderate heating, e.g. to 50° to 150° C. For higher temperatures within this range, the reaction vessel is preferably closed so that the reaction is carried out under autogenous pressure. This makes possible the use of reaction temperatures greater than the boiling point at atmospheric pressure of the solvent used.

Because of the high activity of the organometallic compounds used in the process of the present invention, the reaction times required are usually less than those necessary when an organo-aluminium compound is used. A reaction time of 0.5 to 4 hours is generally satisfactory.

The reaction mixture may be worked up in conventional manner. The excess hydrogen fluoride is preferably first removed, e.g. by reaction with calcium carbonate to give insoluble calcium fluoride or by reaction with potassium fluoride. The thus-insolubilized fluorine compounds are removed, e.g. by filtration, and dilution of the separated reaction medium with water causes the desired product to precipitate. It may then be separated, e.g. by filtration and purified in the usual way, but very often it is sufficiently pure for use in the next stage without additional purification.

The following Examples illustrate the invention.

EXAMPLE 1

Preparation of 2-Deoxy-2-fluoro-1,3,5-tri-O-benzoyl-α-D-arabinofuranose

COMPARATIVE EXAMPLE (Using procedure described in the literature)

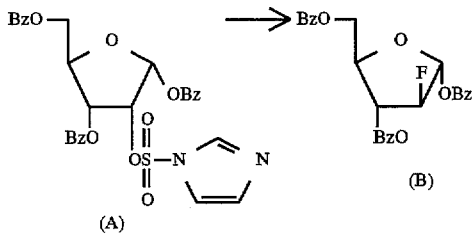

A mixture of 8.2 g of 2-O-(imidazolylsulfonyl)-1,3,5-tri-O-benzoyl-α-D-ribofuranose (see J. Org. Chem., 50, (1985) p.3646) and 4.3 g of $KHF_2$ is added to 41 ml of 2,3-butanediol and 2.0 ml of 50% aqueous HF in a flask vented under nitrogen to a scrubber (scrubbed with 5% NaOH). Heat to 120° C. during 4 hours and follow reaction by HPLC. (Additional heating time will result in product decomposition). Cool to 75° C. and add 40 ml of ethyl acetate and cool to room temperature. Add 60 ml of saturated sodium carbonate solution (significant $CO_2$ evolution). Separate the bottom aqueous layer. Wash organic layer with 60 ml 5% NaCl solution and separate. Perform an azeotropic solvent exchange under vacuum into methanol at 20°–250° C. with approximately 30 ml of methanol at the final stage. Crystallization of the product occurred. Cool to 0°–5° C. and stir two hours to complete the crystallization, filter the crystals and wash with q.s. cold methanol giving 4.03 g (yield 62%, mp=80° C.) of the desired fluoro compound (B).

Process of Invention

A mixture of 8.2 g of the same starting material (A) and 4.88 g (1 mole equivalent) of ferric acetylacetonate is added (under nitrogen) to 50 ml of dioxane and anhydrous hydrogen fluoride (2.2 g, 0.11 moles) was then transferred under nitrogen into the dioxane with continuous stirring. The reaction mixture was then heated to 90° C. over 30 minutes. The reaction mixture was sampled as previously described over the 2 hour reaction period. After 1 hour the compound (B) constituted 85% w/w of the product and the remaining starting material was less than 1%. The reaction mixture was cooled, and the coloured solid present was filtered off. Deionised water (200 ml) was then added to the filtrate, which precipitated out the product. The off-white solid was filtered off, and washed with ice-cold methanol and then dried in a vacuum oven to give an off-white solid (about 5.44 g (yield 85%), mp=81° C., Purity (HPLC)~95.2%).

This demonstrates an improved yield with a short time reaction and low reaction temperature.

EXAMPLE 2

Methyl-5-O-benzyl-2-deoxy-2-fluoro-α-D-arabinofuranoside

COMPARATIVE EXAMPLE (Using procedure as described in the literature: J.O.C, 1969, 2634)

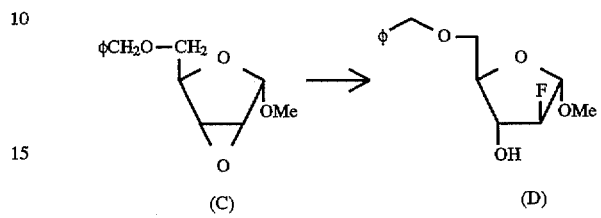

A solution of 7 g of starting material (C) and 15 g of $KHF_2$ in ethylene glycol (140 ml) was refluxed gently for 1 hr. 30 min. (190°–200° C.). The cooled mixture was poured into saturated $NaHCO_3$ (500 ml) and extracted with $CHCl_3$ (3×200 ml). Evaporation gave a syrupy residue where HPLC analysis indicated 3.5 g of the desired product (D) with 1.3 g of still unreacted starting material (C) (81% conversion and 46% yield, i.e. 57% selectivity).

Process of the invention:

A solution of 8 g of (C) (34 mmoles) and 11.97 g of Fe(acac)₃ in dioxane (100 ml) with anhydrous hydrogen fluoride (4.7 g, 8 equivalents), under nitrogen was heated to gentle reflux (100° C.) over 1 hr. The cooled mixture was filtered to remove the solid. Dionised water (300 ml) was then added to the filtrate, which precipitated out the product. The off-white solid was filtered off, washed with ice-cold methanol and then dried in a vacuum oven to give an off-white solid: ~5.1 g (69% yield. Total conversion).

EXAMPLE 3

Cyclohexene oxide (15.2 g 155 m.moles) and Fe(acac)₃ (54.7 g 155 m.moles) were stirred with a 9.5% w/w solution of HF/dioxane in an autoclave at 20° C. Disappearance of the substrate could be monitored by GC analysis. The reaction mixture was filtered and the filter cake washed with further dioxane. The filtrate was then poured into water (160 g) and neutralised with calcium carbonate (56 g). Filtration and washing of the filter cake gave a filtrate containing 2-fluorocyclohexanol (11.2 g), equivalent to a yield of 60.8%. (Determined by GC using cyclohexanol as an internal standard. The crude product could be extracted into a suitable solvent and recovered by distillation under reduced pressure. The product identity was confirmed by gc/ms.)

The same procedure without the use of Fe(acac)₃ gave only a 16.8% yield of 2-fluorocyclohexanol.

We claim:

1. Process for the preparation of a fluoro-compound by reaction of a reactive oxy-acid ester or a reactive cyclic ether other than an anhydrouridine with hydrogen fluoride wherein the reaction is carried out under anhydrous conditions in the presence of an organometallic compound of formula:

$$MY_mZ_n \qquad (I)$$

where M is a 4-, 6-, or 8-coordinated metal wherein said metal is iron, Y is a monodentate ligand, Z is a bidentate ligand or a cyclopentadienyl ligand, and m and n are each zero or positive integers such that (m +2 n)=4, 6 or 8.

2. Process according to claim 1 in which a reactive oxy-acid ester of formula:

$$R_1R_2CHOX \qquad (II)$$

is converted into a fluoride of formula:

$$R_2R_2CHF \qquad (III)$$

wherein X is a sulphonic acid residue and $R_1$ and $R_2$ are each hydrogen or alkyl of 1 to 6 carbon atoms, said alkyl radicals being optionally linked to form a 4 to 7 membered ring and being unsubstituted or substituted by phenyl, halogen, hydroxy, or alkoxy of 1 to 6 carbon atoms.

3. Process according to claim 2 in which —OX is a tosylate, mesylate, triflate, or imidazole-sulfonate residue.

4. Process according to claim 1 in which an epoxide compound of formula:

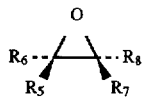 (IV)

is converted into a β-hydroxy-fluoro-compound of formula:

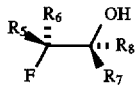 (V)

where $R_5$, $R_6$, $R_7$, $R_8$ may be the same or different, and each represents hydrogen or alkyl of 1 to 12 carbon atoms, optionally linked to form a 4- to 7- membered ring and unsubstituted or substituted by alkyl, aryl or aralkyl substitutents.

5. Process according to claim 1 wherein for said organometallic compound, Y is halogen, alkoxy of 1 to 4 carbon atoms which may be halogenated, or phenoxy optionally substituted by alkyl of 1 to 4 carbon atoms, halogen, or nitro, and Z is a carboxylato radical derived from an alkanoic acid of up to 12 carbon atoms which may be halogenated or from benzoic acid optionally substituted by alkyl or 1 to 4 carbon atoms, halogen or nitro, a radical derived from an alkanesulphonic acid of 1 to 12 carbon atoms, or a β-diketo residue of a compound of formula: R'—COCH$_2$CO—R", where R' is alkyl or haloalkyl of 1 to 4 carbon atoms and R" is hydrogen, hydroxy, alkoxy of 1 to 4 carbon atoms, or alkyl or haloalkyl of 1 to 4 carbon atoms, or a cyclopentadienyl ligand.

6. Process according to claim 5 in which m is 0, n is 3 and Z is a said β-diketo residue.

7. Process according to claim 6 in which Z is acetylacetonato.

8. Process according to claim 1 wherein the reaction is carried out in the presence of an inert organic solvent.

9. Process according to claim 8 in which said solvent is 1,4-dioxane, tetrahydrofuran, 1,2-dimethoxyethane, or bis (2-methoxyethyl)ether.

10. Process according to claim 1 wherein 2 to 20 moles of hydrogen fluoride are used per mole of starting material.

11. Process according to claim 1 wherein 0.5 to 2.0 moles of said organometallic compound are used per mole of starting material.

12. Process according to claim 1 wherein the reaction is operated at 50° to 150° under autogenous pressure.

13. Fluoro-compounds prepared by the process as claimed in claim 1.

14. Fluoro-compounds prepared by the process as claimed in claim 2.

15. Fluoro-compounds prepared by the process as claimed in claim 4.

16. Fluoro-compounds prepared by the process as claimed in claim 5.

* * * * *